(12) United States Patent
Naegerl et al.

(10) Patent No.: US 7,615,082 B2
(45) Date of Patent: Nov. 10, 2009

(54) ARTIFICIAL JOINT

(75) Inventors: Hans Naegerl, Gleichen (DE); Joachim Theusner, Munich (DE); Dietmar Kubein-Meesenburg, Goettingen (DE)

(73) Assignee: HJS Gelenk System GmbH, Munich (DE)

( * ) Notice: Subject to any disclaimer, the term of this patent is extended or adjusted under 35 U.S.C. 154(b) by 746 days.

(21) Appl. No.: 10/946,643

(22) Filed: Sep. 22, 2004

(65) Prior Publication Data
US 2005/0125069 A1    Jun. 9, 2005

Related U.S. Application Data

(63) Continuation of application No. PCT/DE03/00827, filed on Mar. 13, 2003.

(30) Foreign Application Priority Data
Mar. 22, 2002    (DE)    ................................ 102 13 063

(51) Int. Cl.
*A61F 2/66*    (2006.01)
(52) U.S. Cl. .................................. 623/21.18
(58) Field of Classification Search ............. 623/20.15, 623/20.32, 21.13, 21.16, 17.14, 18.11, 19.12, 623/20.22, 21.18, 23.13, 23.4, 47
See application file for complete search history.

(56) References Cited

U.S. PATENT DOCUMENTS

| | | | |
|---|---|---|---|
| 3,839,742 A | 10/1974 | Link | |
| 3,886,599 A | 6/1975 | Schlein | |
| 3,975,778 A | 8/1976 | Newton, III | |
| 4,069,518 A * | 1/1978 | Groth et al. | 623/21.18 |
| 4,156,944 A * | 6/1979 | Schreiber et al. | 623/21.18 |
| 5,282,870 A * | 2/1994 | Moser et al. | 623/20.31 |
| 5,556,432 A | 9/1996 | Kubein-Meesenburg et al. | |
| 5,658,342 A * | 8/1997 | Draganich et al. | 623/20.29 |
| 6,120,543 A | 9/2000 | Kubein-Meesenburg et al. | |
| 6,183,519 B1 | 2/2001 | Bonnin et al. | |
| 2003/0158606 A1 * | 8/2003 | Coon et al. | 623/20.15 |

FOREIGN PATENT DOCUMENTS

| | | |
|---|---|---|
| DE | 2236141 | 1/1974 |
| DE | 42 02 717 | 6/1993 |
| DE | 195 21 597 | 12/1996 |
| FR | 0600806 | * 11/1993 |

* cited by examiner

*Primary Examiner*—Eduardo C Robert
*Assistant Examiner*—David Comstock
(74) *Attorney, Agent, or Firm*—Crowell & Moring LLP

(57) ABSTRACT

An artificial joint (3), particularly for replacing a talocrural joint, including a first primary joint surface (1) that forms an articular fossa (4) particularly for replacing the tibia composed of concave curvatures extending parallel to a primary function plane of the joint (3), which corresponds to the sagittal plane, and a second primary joint surface (2) which cooperates with the first primary joint surface (1) as a component of a condoyle (5) that replaces the talus and has convex curvatures (7, 8, 9, 10) on the primary function plane that are adapted to the first primary joint surface (1). To achieve high stress resistance and optimal joint mobility, depending on the position of the joint, the radii of the curvatures (7, 8, 9, 10) are calculated such that the differential amounts arising between the corresponding radii of the first and second primary joint surfaces (1, 2) in an ascending angular position (V) relative to a descending angular position and also simultaneously between a medial face (11) and a lateral face (12) of the joint (3) deviate from one another.

15 Claims, 2 Drawing Sheets

ARTIFICIAL JOINT

CROSS REFERENCE TO RELATED APPLICATIONS

This application is a continuation of international patent application no. PCT/DE03/00827, filed Mar. 13, 2003, designating the United States of America, and published in German as WO 03/079938 A1 on Oct. 2, 2003, the entire disclosure of which is incorporated herein by reference. Priority is claimed based on Federal Republic of Germany patent application no. DE 102 13 063.9, filed Mar. 22, 2002.

BACKGROUND OF THE INVENTION

This invention relates to an artificial joint which is intended in particular for replacement of an ankle joint and has a first main articular surface which forms a joint socket and is intended in particular for replacement of the tibia, composed of concave curvatures parallel to a main function plane of the joint which corresponds to the sagittal plane and with a second main articular surface which is mechanically linked to the first main articular surface as part of a condyle which replaces the talus in particular with curvatures that are concave in the main function plane and are coordinated with the first main articular surface, in which the radii of the convex curvatures of the second main articular surface are smaller than those of the corresponding curvatures of the first main articular surface.

Artificial joints of this type are used in practice in a variety of ways, e.g., to replace the ankle joint and are therefore known from prior public use. The condyle, as the basic form of such joints, is designed to be spherical or cylindrical, for example, and therefore permits one or more degrees of freedom. The corresponding articular surfaces have a difference which corresponds to the desired tolerance and must, in particular, comply with the requirements for a high load-bearing capacity and a low mechanical wear at the same time.

In medical practice, however, it has been found that the properties of natural joints can be simulated only very inadequately using the known artificial joint. In particular, it is not possible using the known artificial joint to achieve the properties of natural joints which are suitable for transmitting high forces under load while at the same time having a high measure of mobility under reduced loads. As a result, the desired mobility must often be sacrificed in order to achieve increased long-term load-bearing capacity.

SUMMARY OF THE INVENTION

Accordingly, it is an object of the invention to provide an improved artificial joint.

Another object of the invention is to provide an artificial joint which is particularly suited for replacing an ankle joint.

A further object of the invention is to provide an artificial joint which can achieve both high mobility and a high durability or long-term load-bearing capacity at the same time.

A particular object of the invention is to provide an artificial joint which achieves increased freedom of movement without a reduction in long-term load-bearing capacity.

These and other objects are achieved in accordance with the present invention by providing an artificial joint particularly for replacement of an ankle joint, comprising a first main articular surface and a second main articular surface which cooperates mechanically with the first main articular surface as part of a condyle, the first main articular surface forming an articular socket for replacement of the tibia and being composed of a concave curvature parallel to a main function plane of the joint corresponding to the sagittal plane, and the second main articular surface replacing the talus and having convex curvatures in the main function plane coordinated with the first main articular surface; the radii of the convex curvatures of the second main articular surface being smaller than the radii of the corresponding curvatures of the first main articular surface, and the resulting differential amounts of the corresponding radii of the first and second main articular surfaces deviating from one another in an upward-directed angular position (V) of the joint and in a downward-directed angular position (H). Advantageous preferred embodiments are also described hereinafter.

Thus according to this invention an artificial joint is provided in which the radii are such that the resulting differential amounts of the corresponding radii of the first main articular surface and the second main articular surface deviate from one another in an angular position of the joint directed forward and an angular position of the joint directed to the rear. Because of the deviating differential amounts between the angular position of the joint directed toward the front and the rear, an additional degree of freedom is achieved as a function of the angular position, permitting improved mobility without restricting the load-bearing capacity of the joint in other angular positions. For example, the invention makes it possible for the first time for the condyle to be pivotable on an axis centering in the condyle in an angular position that is associated with high differential amounts and additionally to be pivotable on an axis defined by the contact surface between the condyle and the socket, thereby achieving one additional degree of freedom. The position of the different differential amounts in relation to the body depends on the desired load-bearing capacity and, in particular, is lower with a static load (e.g., when standing) than with a dynamic load.

A particularly advantageous embodiment of the present invention is also achieved by having the radii of the convex curvatures of the second main articular surface be 5 to 20% smaller than those of the corresponding curvatures of the first main articular surface. For practical purposes, this achieves an optimal ratio between the desired mobility on the one hand and the load-bearing capacity on the other hand which, in practice, corresponds approximately to a difference of between 1 and 5 mm.

The shaping of the main articular surface could be designed to be uniform over the entire width perpendicular to the main function plane. However, a modification in which the differential amounts of the radii differ from one another between a medial side facing the middle of the body and a lateral side facing the outside of the body with corresponding angular positions of the joint has proven to be particularly promising in practice. In this way, the design of deviating contact surfaces between the medial and lateral sides is facilitated, which results in a comparatively large area of contact, in particular in the range of smaller differential amounts, while the contact area on the opposite side approaches a contact line and therefore promotes mobility. Therefore, the properties of the joint corresponding to the human movement sequence can be implemented. Furthermore, mobility across the main function plane can also be realized without any problem.

Another refinement of the present invention having particular practical relevance is also achieved by the fact that the curvatures of parallel planes of the second main articular surface have radii that decrease from the lateral side toward the medial side of the joint in the forward- and/or upward-directed angular position and at the same time the curvatures of parallel planes of the second main articular surface have radii that decrease from the medial side to the lateral side of the joint in the rearward- and/or downward-directed angular position. This results in a reversal of the characterization of the contact surface between the first and second main articular surfaces based on the plane across the main function plane depending on the angular position of the joint. In this way, the desired degrees of freedom of each individual angular position can be adapted according to the required properties. The two main articular surfaces contact one another in a linear contact which extends approximately perpendicular to the main function plane. Because of the varying radii in the main articular surface, the linear contact between the main articular surfaces in the forward-directed angular position is in a wedge-shape with the tip of the wedge on the medial side and in the posteriorly directed angular position, the linear contact is to be found with the tip of the wedge on the lateral side with a non-positive engagement. The reason for the wedge-shaped contact line is the differing incongruence.

In practice, a modification of the joint has proven to be especially suitable when the curvatures are composed of several individual radii with a steady transition. In this way mechanical wear can be minimized while at the same time a movement sequence that is harmonious for the patient can be achieved.

Another especially advantageous embodiment is obtained when the first main articular surface or the second main articular surface across the main function plane is designed to be wider in the anterior position than in the posterior position. Because of these first and second main articular surfaces which are in the form of wedge segments and in particular the connected lateral surfaces, the joint has only two degrees of freedom in the case of anterior contact in a non-positive manner with the first main articular surface and at the same time posterior mating contact with the second main articular surface. In the case of posterior contact in a non-positive manner with the first main articular surface and anterior mating contact with the second main articular surface, the joint has four degrees of freedom and in the case of massive non-positive engagement it has three degrees of freedom.

In practice a design in which the size ratio of the first main articular surface to the second main articular surface amounts to approximately 2:3 has proven suitable in order to thereby achieve an optimum of the possible degrees of freedom without any significant restriction on load-bearing capacity.

In practice, an embodiment of this invention in which the first main articular surface or the second main articular surface corresponds to a surface section of a rotationally symmetrical body, in particular a cylinder, a cone or a rotational hyperboloid, has proven particularly advantageous to achieve a resulting introduction of force, depending on the force ratios that occur, such that the factorial components of this force permit amplification of the given anatomical factors. In particular, a transition from a convexity to a concavity between the medial and lateral sides permits an inversion of the contact surface between the opposing joint positions and thus the load distribution.

The properties of the joint are surprisingly improved further by the fact that the second articular surface has a convexity on the medial side across the main function plane and optionally the second main articular surface additionally progresses on the lateral side across the main function plane from a convexity into a concavity which approaches the main function plane, whereby the corresponding first main articular surface has a shape which fits it with a minor difference. The first main articular surface has correspondingly inverted associated curvatures whose concavity, if necessary, has corresponding or slightly larger radii and whose convexity, if necessary, has corresponding or slightly smaller radii. The second main articular surface declines steeply toward the medial side from a convex transition to a concavity and then ends in a lateral pole.

The second main articular surface serves to replace the talus in sections. It is also especially advantageous if the first main articular surface as a unit is allocated simultaneously to the tibia and the fibula. In this way, the unit can be attached to the existing structures with little surgical complexity, with the relative position being predetermined by the unit.

However, another especially promising modification of this invention in which the first main articular surface is composed of two structural elements permits independent replacement of individual damaged parts of the joint. These structural elements may be attached elastically, for example, to this end and therefore may have a restricted relative mobility, in particular on exceeding a maximum load. The structural elements are individually connected to the bone structure for this purpose.

In one embodiment which has proven especially suitable, the two structural elements are joined together in a plane that is parallel to the main function plane to thereby obtain a simple plane of separation. One of the structural elements may then be attached separately to the tibia and the fibula.

Various other embodiments and modifications are, of course, possible within the broad scope of the invention.

BRIEF DESCRIPTION OF THE DRAWINGS

The invention will be described in further detail hereinafter with reference to illustrative preferred embodiments shown in the accompanying drawing figures in which.

DETAILED DESCRIPTION OF PREFERRED EMBODIMENTS

Figure 1:
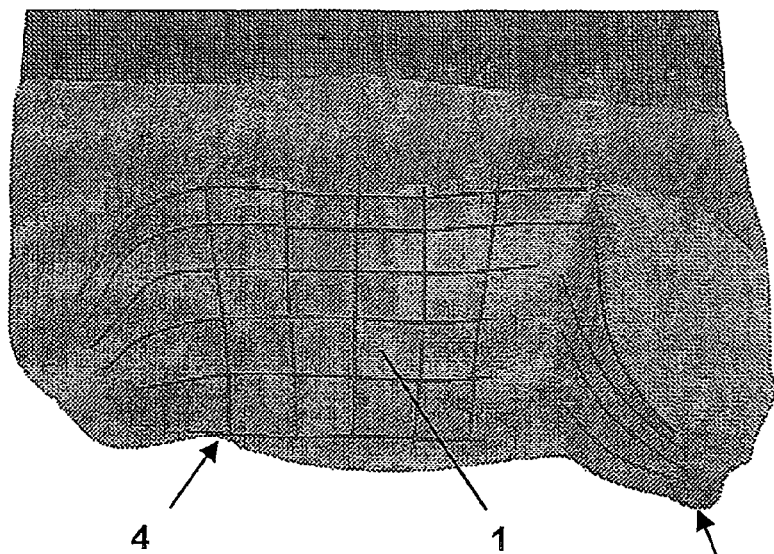
FIG. 1 is a perspective view of a first main articular surface of an artificial joint according to the invention.
Figure 2:
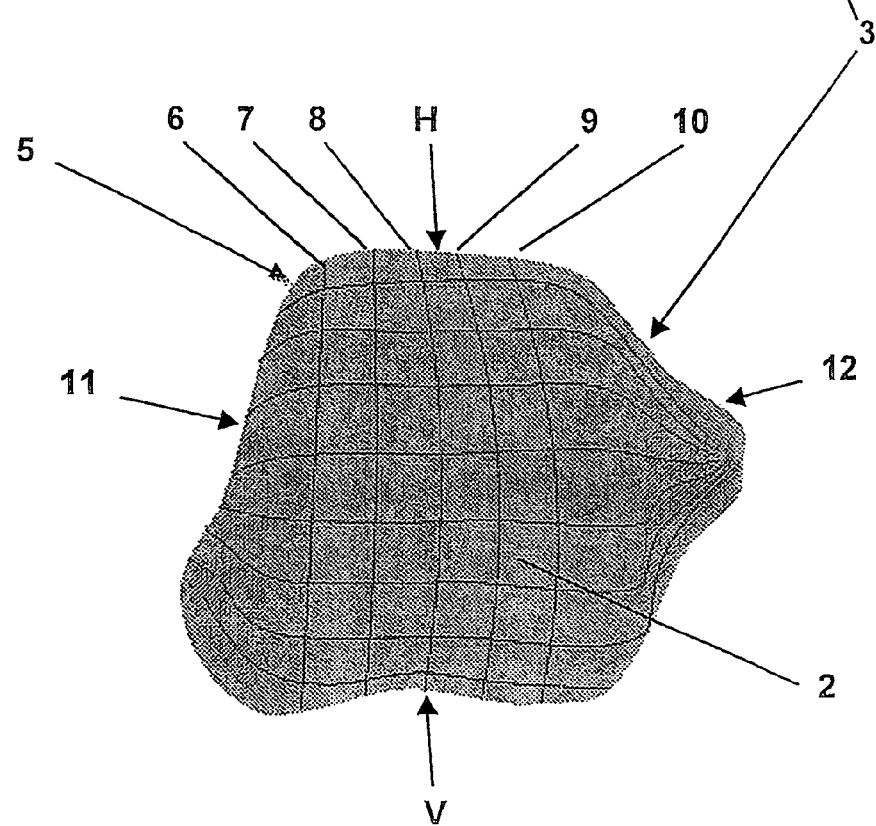
FIG. 2 is a perspective view of a second main articular surface of the artificial joint of the invention.

FIGS. 1 and 2, respectively, show a first main articular surface 1 and a second main articular surface 2 of an artificial joint 3, which is particularly intended for replacement of an ankle joint, the interaction of which is explained in greater detail below with reference to the two figures. The first main articular surface 1 forms a socket 4 due to its largely concave shape and is therefore intended for replacement of the tibia, for example, while a second main articular surface 2 as part of a condyle 5 replacing the talus in particular having a largely convex shape permits mobility with predetermined degrees of freedom. The mobility achieved mainly in this way corresponds to a main function plane of the joint 3. This function plane is perpendicular to the plane of the drawing and corresponds to the sagittal plane. The curvatures 6, 7, 8, 9, 10 of the second main articular surface 2, which are effective here, are labeled in ascending order in the direction from a medial side 11 facing the center of the body to a lateral side 12 facing the outside of the body. The resulting differential amounts of the corresponding radii of the curvatures 6, 7, 8, 9, 10 of the second main articular surface 2 with respect to the first articular surface 1 are designed with dimensions such that their difference differs between 5% and 20% in a particular angular position V of the joint 3 directed forward and/or upward and an angular position H directed downward. At the same time, the curvatures 6, 7, 8, 9, 10 have an increasing radius in the upward-directed angular position V of the medial side 11 of the joint 3 in comparison with the angular upward-directed position V of the lateral side 12, while the curvatures 6, 7, 8, 9, 10 in the angular position H of the medial side 11 of the joint 3 facing to the rear and/or downward have a decreasing radius in comparison with the downward-directed angular position 8 of the lateral side 12.

The first main articular surface 1 and the second main articular surface 2 contact one another along a linear contact surface which is approximately perpendicular to the main function plane of the joint 3. Because of the varying radii of the curvatures 6, 7, 8, 9, 10 of the second main articular surface 2, the linear contact with the first main articular surface 1 in a non-positive engagement is to be found in the upward-directed angular position V in a wedge shape with the tip of the wedge toward the medial side 11 and in the downward-directed angular position H with the tip of the wedge directed toward the lateral side 12. The reason for the wedge-shaped contact line is the difference in incongruence. This simultaneously yields a high load-bearing capacity and optimum mobility of the joint 3 as a function of the respective articular position.

Figure 3:
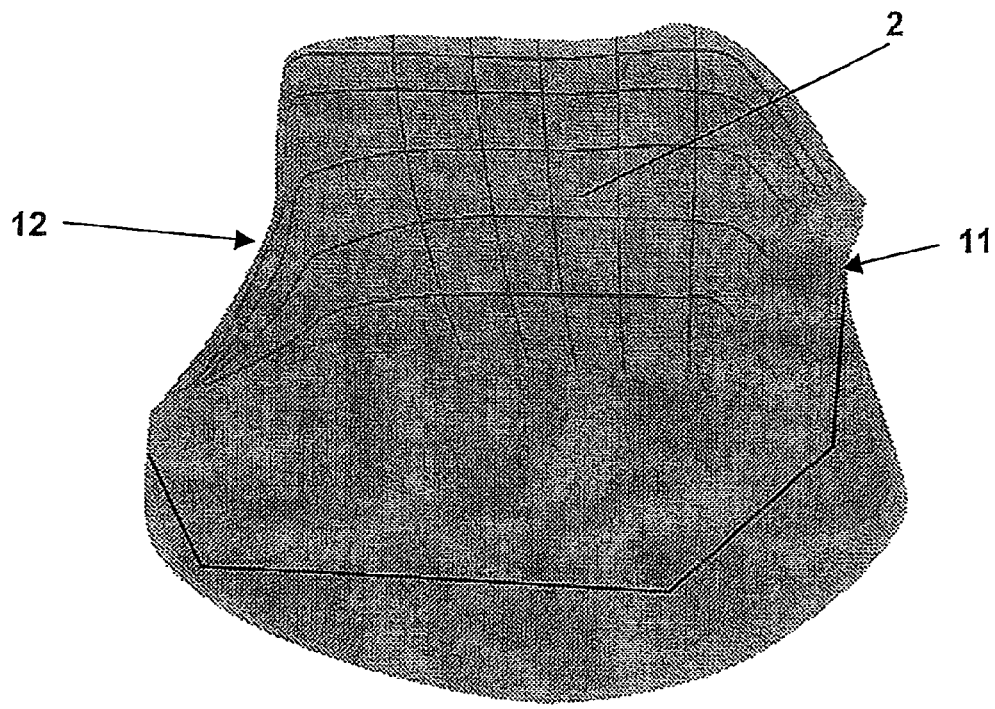
FIG. 3 is a plan view of the second main articular surface.

FIG. 3 shows a top view of the second main articular surface 2 which illustrates in particular the convex transition from the lateral side 12 via a concavity to a convexity of the medial side 11, the second main articular surface 2 declining steeply via a concavity in the remaining course and ending in a lateral pole.

Figure 4:
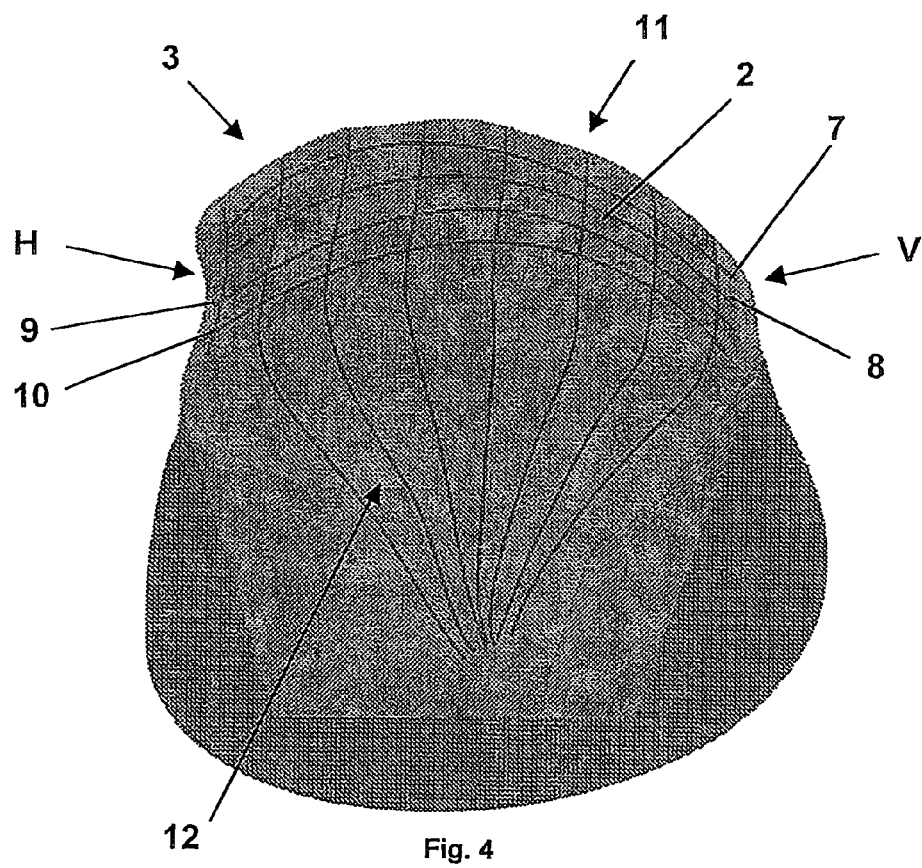
FIG. 4 is a view of the second main articular surface perpendicular to the main functional plane.

FIG. 4 shows the second main articular surface 2 with its curvatures in a view perpendicular to the main function plane. The radii of the curvatures 9, 10, which are designed to be smaller in the upward-directed angular position V on the lateral side 12 than in the downward-directed angular position H, while the radii of the curvatures 7 and 8 on the medial side 11 are greater in the upward-directed angular position V than in the downward-directed angular position H. At the same time, the radii of the curvatures 7, 8, 9, 10 of parallel planes of the second main articular surface 2 decrease from the lateral side 12 of the joint 3 to the medial side 11 in the upward-directed angular position V, and conversely the curvatures 7, 8, 9, 10 have increasing radii in the downward-directed angular position H.

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations within the scope of the appended Claims and equivalents thereof.

What is claimed is:

1. An artificial ankle joint for replacement of an ankle joint in the body, said artificial ankle joint comprising:
   a first main articular surface which forms an articular socket for replacement of the tibia, said first main articular surface being composed of a concave curvature parallel to a main function plane of the joint corresponding to the sagittal plane, and
   a second main articular surface which cooperates mechanically with the first main articular surface as part of a condyle which replaces the talus and has convex curvatures in said main function plane coordinated with the first main articular surface;
   wherein the radii of the convex curvatures of the second main articular surface are smaller than the radii of the corresponding curvatures of the first main articular surface, thereby resulting in differential radii amounts, and
   wherein the resulting differential amounts of the corresponding radii of the first and second main articular surfaces deviate from one another in an upward-directed angular position (V) of the joint and in a downward-directed angular position (H);
   wherein the differential amounts of the radii between a medial side which is directed toward the center of the body and a lateral side which is directed laterally outwardly of the body differ from one another when the angular positions of the joint are the same, and
   wherein on the lateral side the radii of the curvature are smaller in the upward-directed angular position than in the downward-directed angular position, and on the medial side the radii of curvature are greater in the upward-directed angular position than in the downward-directed angular position.

2. An artificial joint according to claim 1, wherein the radii of the convex curvature of the second main articular surface are 5% to 20% smaller than the radii of the corresponding curvatures of the first main articular surface.

3. An artificial joint according to claim 1, wherein the curvatures of parallel planes of the second main articular surface have radii in the upward-directed angular position which decrease from the lateral side to the medial side of the joint.

4. An artificial joint according to claim 1, wherein the curvatures of parallel planes of the second main articular surface have radii in the downward-directed angular position which decrease from the medial side to the lateral side of the joint.

5. An artificial joint according to claim 1, wherein the curvatures are composed of a few individual radii having a smooth transition.

6. An artificial joint according to claim 1, wherein at least one of the first main articular surface and the second main articular surface is wider across the main function plane in an anteriorly-directed angular position than in the downward-directed angular position.

7. An artificial joint according to claim 1, wherein said first main articular surface has a size ratio relative to said second main articular surface of about 2:3.

8. An artificial joint according to claim 1, wherein at least one of the first main articular surface and the second main articular surface has the configuration of a surface cut out of a rotationally symmetrical body.

9. An artificial joint according to claim 8, wherein the surface is configured as a portion of a cylinder or a cone.

10. An artificial joint according to claim 8, wherein the surface is configured as a portion of a rotational hyperboloid.

11. An artificial joint according to claim 8, wherein the surface extends from a convexity on the medial side to a convexity on the second main articular surface via a convexity of the lateral surface, and develops into a steeply descending concavity which opens into a lateral pole.

12. An artificial joint according to claim 1, wherein the corresponding first main articular surface has a shape which is adapted to the second main articular surface with a slight dimensional difference.

13. An artificial joint according to claim 1, wherein the first main articular surface is engaged simultaneously as a unit with both the tibia and fibula.

14. An artificial joint according to claim 1, wherein the first main articular surface is composed of two structural elements.

15. An artificial joint according to claim 14, wherein the two structural elements are joined together in a plane that is parallel to the main function plane.

* * * * *

UNITED STATES PATENT AND TRADEMARK OFFICE
CERTIFICATE OF CORRECTION

PATENT NO. : 7,615,082 B2 Page 1 of 1
APPLICATION NO. : 10/946643
DATED : November 10, 2009
INVENTOR(S) : Naegerl et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1227 days.

Signed and Sealed this

Nineteenth Day of October, 2010

David J. Kappos
*Director of the United States Patent and Trademark Office*